United States Patent

Rakoczi et al.

[11] 4,065,450
[45] Dec. 27, 1977

[54] PROCESS FOR PREPARING 2-GUANIDINOMETHYL-PERHYDROAZOCINE-SULFATE

[75] Inventors: József Rákoczi; Iván Beck; Csaba Kiss; Imre Horváth; Miklós Nemes, all of Budapest, Hungary

[73] Assignee: Egyt Gyogyszervegyeszeti Gyar, Budapest, Hungary

[21] Appl. No.: 661,613

[22] Filed: Feb. 26, 1976

[30] Foreign Application Priority Data

Feb. 27, 1975 Hungary .............................. EE 2313

[51] Int. Cl.² ........................................... C07D 223/04
[52] U.S. Cl. ............................................... 260/239 B
[58] Field of Search ..................... 260/239 B, 583 M

[56] References Cited

U.S. PATENT DOCUMENTS

| | | | |
|---|---|---|---|
| 2,636,901 | 4/1953 | Tindall | 260/583 M |
| 3,187,046 | 6/1965 | Curtis | 260/583 M |

FOREIGN PATENT DOCUMENTS

155,990   7/1968   Hungary .......................... 260/239 B

OTHER PUBLICATIONS

Patai et al., "Chem. of Carbon-Nitrogen Double Bond, pp. 64–65; 468–469.
V. V. Perekalin, "Unsaturated Nitro Compounds," O, Jerusalem, 1964, pp. 168–169.

Marvel et al., J. Amer. Chem. Soc. 68, pp. 185–187,)1946).

*Primary Examiner*—Donald G. Daus
*Assistant Examiner*—Mark L. Berch
*Attorney, Agent, or Firm*—Young & Thompson

[57] ABSTRACT

The invention relates to a novel process for preparing 2-guanidinomethyl-perhydroazocine-sulfate of formula I

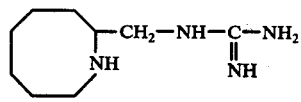

comprising the steps of catalytically reducing the 2-nitromethylene-perhydroazocine of formula IV

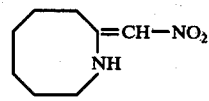

in solution in acetone at a temperature of 20° to 50° C, treating the separated reaction product with an aqueous mineral acid and then reacting it with S-methyl-isothiocarbamid-sulfate.

The process gives the desired end-product of formula I also on industrial scales.

3 Claims, No Drawings

PROCESS FOR PREPARING 2-GUANIDINOMETHYL-PERHYDROAZOCINE-SULFATE

This invention relates to a novel process for preparing 2-guanidinomethyl-perhydroazocine-sulfate of the formula I

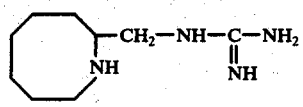   (I)

have hypotensive properties. 2-guanidinomethyl-perhydroazocine can be prepared by reacting the 2-aminomethyl-perhydroazocine of formula III

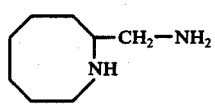   /III/ with S-methyl isothiocarbamide. From the point of wiew of the economy of this process it is of decisive importance the method of preparation of the 2-aminomethyl-perhydroazocine of formula III. The latter compound can be prepared according to the Hungarian patent specification No. 156,590 by reducing the 2-nitromethylene-perhydroazocine of formula IV

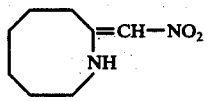   IV

This reduction, however, can be carried out only difficultly and with low yields. Namely, although the reduction carried out with lithium aluminium hydride in tetrahydrofuran gives the 2-aminomethyl-perhydroazocine with a yield of 71% in case of using one mole of the starting compound, the yield abruptly decreases with increase of the amount of the starting compound and in case of using 6 moles of the 2-nitromethylene-perhydroazocine the yield amounts only to 45%. Besides, the use of the lithium aluminium hydride on an industrial scale causes a difficult problem from the point of view of working security.

If according to a further known process variant the reduction is carried out by catalytic hydrogenation, the yields are extremely low even when using one mole of the 2-nitromethylene perhydroazocine on a laboratory scale. Thus the yield amounts to only 26.5 % when using a palladium catalyst on charcoal. With a Raney-nickel catalyst yields of about 30 to 35% can be attained in a benzene solution and yields of about 25 to 30% are obtainable in isopropanol as solution.

Consequently, neither variant of the known reduction process is suitable for the economic production of the 2-guanidinomethyl perhydroazocine of formula I on industrial scales.

Now it has been found that the 2-/N-isopropylidene-aminomethyl/-perhydroazocine of formula II

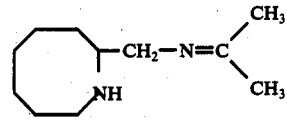   /II/ can be obtained by catalytically hydrogenating the 2-nitromethylene-perhydroazocine of formula IV in solution in acetone at temperatures between 20° C and 50° C. After separating and treating with an aqueous mineral acid, such as sulfuric acid, the thus-obtained 2-/N-isopropylidene-aminomethyl/-perhydroazocine can be directly transformed into 2-guanidinomethyl-perhydroazocine-sulfate by treating it with S-methyl-isothiocarbamid-sulfate.

Catalysts generally used in catalytic hydrogenation, such as palladium on charcoal, Raney-nickel, platinum-oxide etc., can be used in the hydrogenation process.

According to a preferred embodiment of the process of the invention the 2-nitromethylene-perhydroazocine is hydrogenated in solution in acetone in the presence of a Raney-nickel catalyst at a temperature of from 20° to 30° C. The thus-obtained 2-/N-isopropylidene-aminomethyl/-perhydroazocine is treated after separation with an aqeous mineral acid and then transformed into 2-guanidinomethyl-perhydroazocine by treating with S-methyl-isothiocarbamide-sulfate.

The 2-/N-isopropylidene-aminomethyl/-perhydroazocine used as intermediary compound is novel and can be transformed into the product of formula I with yields of about 70%.

The starting compound of formula IV can be prepared by reacting 2-methoxy-perhydroazocine with nitromethane.

The process according to the invention can be advantageously used for preparing the compound of formula I on industrial scales because it enables the reduction even of 150 to 180 moles of 2-nitromethylene-perhydroazocine with a yield of 67%, and the thus-obtained compound of formula II can be transformed with the claimed process into the desired end-product of formula I with yields exceeding 70%.

The process according to the invention is further illustrated by the aid of the following non-limiting Examples.

EXAMPLE 1

In a solution of 170 g. of 2-nitromethylene-perhydroazocine in 2000 ml. of acetone 170 g. of Raney-nickel catalyst are suspended. Previously the catalyst is dehydrated with 100 ml. of isopropanol. The suspension in acetone is hydrogenated for 24 hours at a temperature of 20° to 25° C under a pressure of 40 to 45 atm. Thereafter the reaction mixture is filtered and evaporated under a pressure of 40 torr., at a maximum vapour temperature of 50° C. 200 ml. acetone are added to the residue of evaporation, and the mixture is refluxed for 2 hours. Thereafter the mixture is again evaporated under a pressure of 40 torr at a vapour temperature of 50° C. The residue of evaporation is distilled off under a pressure of 9 torr at a vapour temperature between 109° C and 110° C.

In this way 136 g./74%/ of 2-/N-isopropylidene-aminomethyl/-perhydroazocine are obtained.

250 ml. of water are fed into a three neck round flask provided with a mixer, a thermometer and a reflux cooler. 36.5 g. of concentrated sulfuric acid are added while stirring and cooling, whereafter the 136 g. of 2-/isopropylidene-aminomethyl/-perhydroazocine prepared in the above-described way are fed into the flask. The mixture is warmed until boiling during about an hour, whereafter 130 ml. of aqueous acetone are distilled off until reaching a vapour temperature of 100° C. The mixture is cooled to 30° C and then 102 g. of S-methyl-isothiocarbamide-sulfate are added. The mixture is warmed to 100° C under stirring in 2 hours. The methyl mercaptane being formed in the reaction is absorbed in an aqueous solution of 400 g. of sodium hypochlorite. The reaction mixture is boiled for 1 hour at 100° C, then it is cooled to 10° C, filtered and washed with 4×50 ml. of ethanol. The wet substance is recrystallized from 400 ml. of distilled water, filtered and dried. The thus-obtained product weighs 155 g. 300 ml. of water are distilled off from the aqueous mother liquor, and after cooling to 20° C 100 ml. of ethanol are added. The thus-obtained product weighs 13 g. The total yield amounts to 168 g. /76,4%/ of 2-guanidinomethyl-perhydroazocine-sulfate with a melting point of 240°–242° C.

EXAMPLE 2

Into a dehydrated hydrogenating apparatus having a volume of 1000 liter 560 kg. of acetone containing in dissolved state 30 kg. of 2-nitromethylene-perhydroazocine are introduced. 30 kg. of Raney-nickel catalyst are suspended in 20 kg. of isopropanol at 0° C, and after sedimenting and decanting the liquid, the dehydration of the catalyst is repeated with further 20 kg. of isopropanol at 0° C. Thereafter the catalyst is suspended in 20 kg. of isopropanol and the suspension is sucked into the reaction mixture contained in the hydrogenating apparatus. The free space in the hydrogenating apparatus is rinsed with nitrogen and then the reaction mixture is stirred under hydrogen atmosphere for 20 hours at 20° to 25° C under a pressure of 40 to 45 att. After finishing the hydrogenation the catalyst is filtered off from the acetone suspension, and the solution free from catalyst is evaporated under a pressure of 40 torr. at a maximum vapour temperature of 60° C. The thus-obtained distillation residue is boiled with 160 kg. of anhydrous acetone for an hour and then again evaporated under a pressure of 40 torr. at a maximum vapour temperature of 60° C. The evaporation residue is fractionated under a pressure of 3 torr. at a vapour temperature of 90° to 95° C. In this way, 21.5 kg. /67%/ of distilled 2-/N-isopropylidene-aminomethyl/-perhydroazocine are obtained.

150 liter of water, 86 kg. of 2-/N-isopropylidene-aminomethyl/-perhydroazocine and 22.5 kg. of concentrated sulfuric acid are fed into an enamelled apparatus having a volume of 250 liter and provided with a zinced mixer. The reaction mixture is warmed in half an hour until boiling while stirring, and 30 kg. of aqueous acetone are distilled off until reaching a vapour temperature of 100° C. The mixture is cooled to 30° C, then 64 kg. of S-methyl-isothiocarbamide-sulfate are added. The reaction mixture is warmed during 2 hours to 100° C. The methyl-mercaptane being formed in the reaction is oxidized with 300 kg. of sodium hypochlorite. The reaction mixture is boiled under stirring at a temperature of 100° C for an hour, then cooled to 10° C, filtered and washed with 80 kg. of ethanol. The wet 2-guanidinomethyl-perhydroazocine-sulfate is dissolved in 300 liter of distilled water at 100° C. After clarifying and filtering the solution is cooled to 0° C, whereupon white crystals separate from the aqueous solution. After filtering and drying 88 kg. of end-product are obtained. 200 liter of water are distilled off from the aqueous mother liquour and 80 liter of ethanol are added the distillation residue. The crystallizing material is filtered and dried. In this way 13 kg. of product are obtained. Total yield: 101 kg. /71% / of 2-guanidinomethyl-perhydroazocine-sulfate; m.p.: 240°–242° C.

EXAMPLE 3

170 g. of Raney-nickel catalyst are suspended in a solution of 170 g. of 2-nitromethylene-perhydroazocine in 2000 ml. of acetone. Previously, the catalyst is dehydrated with 100 ml of isopropanol. The suspension in acetone is hydrogenated for 24 hours under a pressure of 40 to 45 atm. at a temperature of 20° to 25° C, then it is filtered and the filtrate is evaporated under a pressure of 40 torr at a maximum vapour temperature of 50° C. The evaporation residue is distilled off under a pressure of 9 torr at a vapour temperature between 105° C and 110° C. The distilled product weighs 125 g. /72%/ and contains 80% of 2-/N-isopropylidene-aminomethyl/-perhydroazocine and 20% of 2-aminomethyl-perhydroazocine.

Thereafter one proceeds as described in Example 1. Total yield: 168 g. /76.4% / of 2-guanidinomethyl-perhydroazocine-sulfate; m.p.: 240°–242° C.

What we claim is:

1. A novel process for preparing 2-guanidinomethyl-perhydroazocine-sulfate of formula I

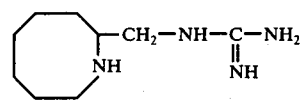

by catalytical reduction of 2-nitromethylene-perhydroazocine of formula IV

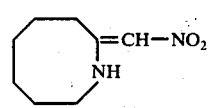

and reacting the thus-obtained product with S-methyl-isothiocarbamide-sulfate, characterized in that the 2-nitromethylene-perhydroazocine is hydrogenated in solution in acetone at a temperature of 20 to 50° C, whereafter the separated reaction product is treated with an aqueous mineral acid and then reacted with the S-methyl-isothiocarbamid-sulfate.

2. A process as claimed in claim 1, in which the catalytic hydrogenation is carried out at a temperature of 20° to 30° C.

3. A process as claimed in claim 1, in which the hydrogenation is carried out in the presence of Raney-nickel catalyst.

* * * * *